United States Patent [19]

Casagrande et al.

[11] Patent Number: 5,047,425
[45] Date of Patent: Sep. 10, 1991

[54] AMINE DERIVATIVES HAVING CARDIOVASCULAR ACTIVITY

[75] Inventors: Cesare Casagrande, Arese; Francesco Santangelo; Luisa Calabi, both of Milan, all of Italy

[73] Assignee: Simes Societa Italiana Medicinali & Sintetici SpA, Vicenza, Italy

[21] Appl. No.: 278,205

[22] Filed: Nov. 30, 1988

[30] Foreign Application Priority Data

Dec. 1, 1987 [IT] Italy ............... 22824 A/87

[51] Int. Cl.$^5$ ............. A61K 31/275; A61K 31/235; A61K 31/24; A61K 31/19; A61K 31/435; A61K 31/495; C07C 255/03; C07C 321/00; C07C 233/00; C07D 241/04

[52] U.S. Cl. .................. 514/522; 514/524; 514/561; 514/562; 514/563; 514/564; 514/566; 514/579; 514/613; 514/616; 514/618; 514/619; 514/620; 514/648; 514/652; 514/237.5; 514/237.8; 514/255; 514/315; 514/327; 514/328; 558/303; 558/412; 558/413; 558/414; 558/415; 558/416; 558/419; 558/422; 562/426; 562/427; 562/430; 562/432; 562/448; 562/453; 564/1; 564/123; 564/152; 564/154; 564/155; 564/157; 564/162; 564/163; 564/165; 564/349; 564/350; 564/351; 544/382; 544/383; 544/384; 544/385; 544/159; 544/162; 544/163; 544/168; 546/215; 546/216; 546/219; 546/220; 546/221

[58] Field of Search .............. 558/303, 412, 413, 414, 558/415, 416, 419, 422; 562/426, 427, 430, 432, 448, 453; 564/123, 152, 154, 155, 157, 162, 163, 165, 1, 349, 350, 351; 514/652, 648, 561, 562, 563, 564, 566, 618, 619, 620, 613, 616, 579, 522, 524

[56] References Cited

U.S. PATENT DOCUMENTS 4,829,085 5/1989 Wenderoth et al. ............. 558/412

Primary Examiner—Mary C. Lee
Assistant Examiner—J. Richter
Attorney, Agent, or Firm—Cushman, Darby & Cushman

[57] ABSTRACT

Compounds of the formula

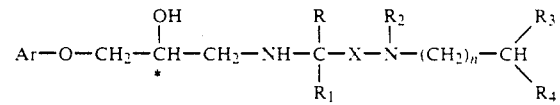

wherein Ar, R, $R_1$, $R_2$, $R_3$, $R_4$, X and n have the meanings mentioned in the description, processes and intermediates for their preparation, pharmaceutical compositions which contain them and their use in therapy in the treatment of cardiovascular diseases.

5 Claims, No Drawings

AMINE DERIVATIVES HAVING CARDIOVASCULAR ACTIVITY

DESCRIPTION

The present invention relates to compounds having beta-blocking activity, pharmaceutically acceptable salts thereof, processes and intermediates for their preparation, their therapeutic use and pharmaceutical compositions containing them.

The beta-blocking drugs are used in therapy owing to their effectiveness in cardiovascular disorders and in particular in hypertension, angina pectoris and heart arrhythmia (Goodman and Gilman—The Pharmacological Basis of Therapeutics—7th Edition—Macmillan Publishing Company—1985). The numerous studies on the structural model of beta-blocking drugs have shown that for the activity to be exhibited, the presence is essential of an aromatic and heteroaromatic system connected directly or by means of an oxymethylene bridge to an alpha-hydroxyethylamino group (György Szasz—Pharmaceutical Chemistry of Adrenergic and Cholinergic Drugs—CRC Press Inc., 1985). The most active and therapeutically more utilized beta-blockers belong to the structural type containing the oxymethylene bridge. Examples among the most common beta-blockers are Alprenolol (Merck Index —10th Edition, No. 304), Atenolol (Merck Index—10th Edition, No. 868), Carteolol (Merck Index—10th Edition, No. 1850), Metoprolol (Merck Index—10th Edition, No. 6027), Nadolol (Merck Index—10th Edition, No. 6195), Oxprenolol (Merck Index —10th Edition, No. 6820), Pindolol (Merck Index—10th Edition, No. 7317), Propranolol (Merck Index—10th Edition, No. 7740), Timolol (Merck Index—10th Edition, No. 9284).

On the other hand, the basic features of the beta-blocking drugs, which are the basis for their use in the above pathologies, and in particular that of moderating the cardiac activity and of protecting if from sympathetic stimuli, either direct or reflex mediated, have as a counterpart a decrease of the cardiac output and an increase of the vascular resistances which, in endangered cardiovascular situations and in older people, imply the risk of precipitating a situation of cardiac decompensation due to an eccessive decrease of the cardiac contractility and rate (Circulatory Effects and Clinical Uses of Beta-Adrenergic Blocking Drugs—Donald C. Harrison, Editor —Excerpta Medica, 1971).

We have now surprisingly found, and this is an object of the present invention, a new class of compounds structurally correlated to the beta-blocking drugs of the formula

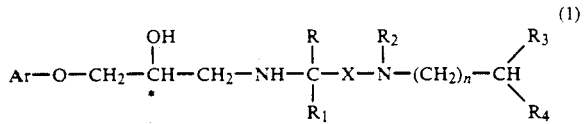

wherein
Ar is a cyclic or bicyclic aromatic or heteroaromatic system optionally substituted by one or more substituents selected among halogens, hydroxy, $C_1$-$C_5$ alkyl, $C_2$-$C_5$ alkenyl, $C_1$-$C_5$ alkoxy, $C_1$-$C_3$ alkylthio, $C_2$-$C_5$ alkenyloxy, or alkoxy-alkyl having from 1 to about 5 carbon atoms both in the alkyl and in the alkoxy portion, optionally with an unsaturation in the chain, phenoxy or phenylalkoxy groups, aminocarbonylalkyl groups having from 1 to 3 carbon atoms in the alkyl portion, cyano, carboxy, aminocarbonyl or amino groups;

R and $R_1$, equal or different from one another, are hydrogen or $C_1$-$C_3$ alkyl;

X is a $(CH_2)_pY$ group wherein Y is a methylene group or a carbonyl group and p is an integer selected among 0, 1 and 2;

$R_2$ is hydrogen or $C_1$-$C_3$ alkyl;

n is an integer selected among 0, 1 and 2;

$R_3$ and $R_4$, equal or different one from the other, are phenyl optionally substituted by one or more halogen, $C_1$-$C_3$ alkyl, $C_1$-$C_3$ alkoxy, nitro, alkylthio, alkylsulfinyl and alkylsulfonyl, having from 1 to 3 carbon atoms in the alkyl portion.

The compounds of formula 1 have at least one asymmetric carbon atom (marked with an asterisk) and can exist in the form of a racemic mixture or of individual isomers or of isomeric mixtures.

The individual isomers are obtained by stereoselective synthesis or by separation from the isomeric mixture according to usual techniques.

An object of the present invention is to provide the compounds of formula 1 both in the form of isomeric mixtures and in the form of individual isomers.

A further object of the present invention is to provide the salts of the compounds of formula 1 with pharmaceutically acceptable organic or inorganic acids as well as the salts with organic or inorganic bases acceptable for pharmaceutical use, of the compounds of formula 1 wherein Ar is an acid function (for example when Ar contains a phenolic hydroxy or a carboxy group).

Examples of acids and bases useful as salifying agents are hydrochloric acid, sulphuric acid, tartaric acid, sodium or potassium hydroxide.

The compounds of formula 1 according to the present invention are endowed with beta-blocking activity without, however, showing the side effects of the class such as a decrease of the cardiac output and the increase of the vascular resistances.

The compounds of the present invention perform part of their action by acting as total or partial antagonists of the beta-adrenergic receptors, but possess additional properties which make them particularly useful in therapy.

Some of these additional properties can be correlated to an activity of a calcium-antagonist type such as, for example, the effects on the vessel and heart cells both at the level of the transmembrane channels and in the intracellular mechanisms.

This gives rise to a number of hemodynamic effects characterized by the reduction of the vascular resistances; in this way the decrease in the cardiac output is avoided while the systemic perfusion is improved, avoiding the risk of cardiac decompensation; in addition, the coronary perfusion is improved with advantage in the therapy of angina pectoris and of coronary diseases in general.

It is also worth noting that, surprisingly, the compounds of formula 1 of the present invention, increase the protection of the cardiac and vascular tissues against ischemic and atherosclerotic damage.

Preferred compounds of formula 1 are those wherein Ar is an aromatic and heteroaromatic system such as phenyl, naphthyl, benzofuryl, 3,4-dihydro-carbostyryl, benzopyranyl, tetrahydronaphthyl, indolyl, indenyl, 1,2,5-thiadiazolyl optionally substituted. Possible substituents of these systems include one or more atoms of chlorine, fluorine or bromine, and allyl, methyl, phenyl, methoxy, allyloxy, cyano, carbamoylmethyl, hydroxy, acetyl, cyclohexyl, methoxyethyl, methylthio, piperazinyl, piperindinyl, morpholyl groups ; R and $R_1$; equal to or different from one another, are hydrogen or methyl; $R_3$ and $R_4$, equal to or different from one another, are phenyl optionally substituted by a fluorine atom.

Specific examples of the above-mentioned substituted aryls are 2-methoxyphenyl, 2-allyloxyphenyl, 2-cyanophenyl, 2-methylphenyl, 2-allylphenyl, 4-carbamoylmethylphenyl, 4-hydroyphenyl, 4-morpholin-1,2,5-thiazodiazol-3-yl, indol-4-yl and 3,4-dihydro-1(H)-carbostyr-5-yl.

Specific examples of compounds of formula 1 are the following:

2-[2-hydroxy-3-(2-methoxyphenoxy)-propylamino]-2-methyl-N-(2,2-diphenylethyl)-N-methyl-propylamine dihydrochloride 2-[2-hydroxy-3-(2-propoxyphenoxy)-propylamino]-2-methyl-N-(2,2-diphenylethyl)-N-methyl-propylamine 2 -[2-hydroxy-33(2-methoxyphenoxy)-propylamino]-2-methyl-N-diphenylmethyl-N-methyl-propylamine 2-[2-hydroxy  3-(2-cyanophenoxy)-propylamino]-2-methyl-N-diphenylmethyl-N-methyl-propylamine 2-{hydroxy-3-[4-92-methoxyethyl)-phenoxy]-propylamino}-2-methyl-N-diphenylmethyl-N-methyl-propylamine 2-[2-hydroxy-3-(2-methoxyphenoxy)-propylamino]-2methyl-N-[2-(4-chlorophenyl)-2-phenyl-ethyl]-N-methyl-propylamine 2-[2-hydroxy-3-(4-carbamoylmethylphenoxy)-propylamino]-2-methyl-N-diphenylmethyl-N-methyl-propylamine 2-[2-hydroxy-3-(4-phenylmethoxy-phenoxy)-propylamino]-2-methyl-N-diphenylmethyl-N-methyl-propylamine 2-[2-hydroxy-3-(2-methoxyphenoxy)-propylamino]-N-diphenylmethyl-N-methyl-propylamine 2-[2-hydroxy-3-(2-methoxyphenoxy)-propylamino]-N-di-(2-chlorophenyl)-methyl-N-methyl-propylamine 2-[2-hydroxy-3-(2-methoxyphenoxy)-propylamino]-2-methyl-N-diphenylmethyl-propylamine 2-[2-hydroxy-30(2-methoxyphenoxy)-propylamino]-2-methyl-N-(3,3-diphenylpropyl)-N-methyl-propylamine N-{2-[2-hydroxy-3-(2-methoxyphenoxy)-propylamino]-ethyl}-N-methyl-(3,3-diphenyl)-propylamine 2-[2-hydroxy-3-(2-methoxyphenoxy)-propylamino]-N-diphenylmethyl-N-methyl-ethylamine 2-[2-hydroxy-3-(2-methoxyphenoxy)-propylamine]-2-methyl-N-diphenylmethyl-N-methyl-propanamide hydrochloride 2-[2-hydroxy-3-(2-methoxyphenoxy)-propylamino]-2-methyl-N-[di(4-fluorophenyl)-methyl]-N-methyl-propanamide 2-[2-hydroxy-3-(2-methoxyphenoxy)-propylamino]-2-methyl-N-[di-(4-bromophenyl)-methyl]-N-methyl-propylamine 2-[2-hydroxy-3-(2-methoxyphenoxy)-propylamino]-2-methyl-N-[di-(4-fluorophenyl)-methyl]-N-methyl-propylamine 2-[2-hydroxy-3-(4-hydroxyphenoxy)-propylamino]-2-methyl-N-diphenylmethyl-N-methyl-propylamine 2-[2-hydroxy-3-(3-aminocarbonyl-4-hydroxyphenoxy)-propylamino]-2-methyl-N-diphenylmethyl-N-methyl-propylamine 2-[2(R)-hydroxy-3-(2-methoxyphenoxy)-propylamino]-2-methyl-N-diphenylmethyl-N-methyl-propylamine.

2-{2-hydroxy-3-[(naphth-5-yl)-oxy]-propylamino]-2-methyl-N-diphenylmethyl-N-methyl-propylamine 2-{2-hydroxy-3-[(3-cyano-pirid-2-yl)-oxy]-propylamino-2-methyl-N-diphenylmethyl-N-methyl-propylamine 2-{2-hydroxy-3-[(3,4-dihydro-1(H)-carbostyrul-5-yl)oxy]-propylamino}-2-methyl-N-diphenylmethyl-N-methyl-propylamine 3-[2-hydroxy-3-(2-methoxyphenoxy)-propylamino]-3-methyl-N-diphenylmethyl-N-methyl-butylamine 3-[2-hydroxy-3-(2-methoxyphenoxy)-propylamino]-3-methyl-N-diphenylmethyl-N-methyl-butanamide 2-[2-hydroxy-3-(2-methoxyphenoxy)-propylamino]-2-methyl-N-[(4-nitrophenyl)-(4-chlorophenyl)-methyl]-N-methyl-propylamine 2[2-hydroxy-3-(2-methoxyphenoxy)-propylamino]-2-methyl-N-[(4-methoxyphenyl)-phenylmethyl]-N-methyl-propylamine 2-[2-hydroxy-3-(2-methoxyphenoxy)-propylamino]-2-methyl-N-[di-(methoxyphenyl)-methyl]-N-methyl-propylamine 2-[2-hydroxy-3-(2-allylphenoxy)-propylamino]-2-methyl-N-diphenylmethyl-N-methyl-propylamine 2-[2-hydroxy-3-(4-chloro-2-methoxyphenoxy)-propylamino]-2-methyl-N-(diphenylmethyl)-N-methyl-propylamine.

The preparation of the compounds of formula 1 is a further object of the present invention.

Useful intermediates are the amines of the formula

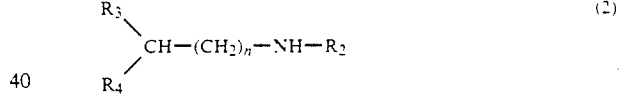

wherein $R_2$, $R_3$, $R_4$ and n have the meanings already mentioned, which are known compound or compounds easily prepared with known techniques (A.I. Meyers. G. Erik Jagdmann Jr., J. Am. Chem. Soc., Vol. 104, No. 3, 1982, page 877).

The compounds of formula 2 are condenses directly with an aminoacid, in the presence of a condensing agent such as dicyclohexylcarbodiimide, or with a suitable derivative of the aminoacid itself of the formula:

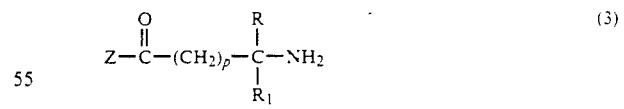

wherein R, $R_1$ and p have the meanings already mentioned and Z is hydroxy or chlorine, to yield the compounds of the formula

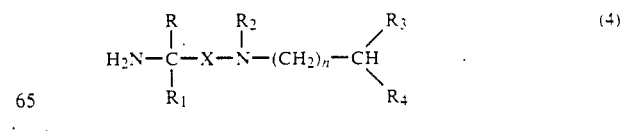

wherein R, $R_1$, $R_2$, $R_3$, $R_4$, n and p have the meanings already mentioned and X is a $(CH_2)_p$—CO group.

It is clear to a man skilled in the art that the condensation reaction, where necessary, implies the protection of the amino group of the aminoacid derivative (3), according to known techniques.

The protection will, for example, be accomplished by means of a cyclic imide such as the phthalimide or with protective groups such as benzyl or benzyloxycarbonyl groups.

The condensation of the protected aminoacid derivative (3) with the amine of the formula (2) is performed according to known methods and yields the compounds 4[X=(CH$_2$)$_p$—CO] wherein the primary amino group is protected.

The protective group is removed by catalytic hydrogenation or by treatment with acids or, in the case of cyclic imides, by treatment with hydrazine or by reduction with sodium borohydride in aqueous solvents and subsequent acid hydrolysis; the compounds of formula (4) are thus obtained.

A further process for the preparation of compounds of formula 4, wherein one or both of the substituents R and R$_1$ are hydrogen, consists in the introduction of the amino group either directly by nucleophilic substitution with ammonia starting with the ethylamine of the formula

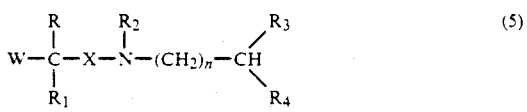

wherein X, R$_2$, R$_3$, R$_4$ and n have the meanings already mentioned and W is chlorine, bromine, mesyloxy or p.tolysulfonyloxy, or by hydrolysis of a phthalimide obtained by reacting a compound 5 with potassium phthalimide.

The preparation of compounds of formula 4 in which X is a (CH$_2$)$_p$CH$_2$ group is performed according to several alternative synthesis procedures.

A first synthesis procedure comprises the reduction of the compound (4) wherein X is a (CH$_2$)$_p$CO group.

The reduction reaction is carried out with metal hydrides such as lithium and aluminium hydride or with diborane optionally in the form of a complex, in an inert organic solvent such as ethyl ether, tetrahydrofuran dimethoxyethane at a temperature of from 0° C. to the boiling temperature of the reaction mixture.

As an alternative the compounds of formula 4 wherein X is (CH$_2$)$_p$CH$_2$ and p is 0 are prepared from the compounds of formula 2 by condensation with suitable nitroalkanes of the formula

wherein R and R$_1$ have the meanings already mentioned, in the presence of formaldehyde, which can also act as a solvent, and subsequent reduction of the nitro group by catalytic hydrogenation or by treatment with metal hydrides.

The compounds of formula 4 are new and are a further object of the present invention.

The preparation of the compounds of formula 1 from the intermediate 4 comprises the reaction with an epoxide of the formula

wherein Ar has the meaning already mentioned; or with a chlorohydrin of the formula

wherein Ar has the meaning already mentioned.

The reaction of the compounds 4 with the epoxide 7 or with the chlorohydrin 8 yields the compounds of formula 1 and is performed in a suitable inert organic solvent at a temperature of from room temperature to the reflux temperature of the reaction mixture.

Examples of suitable organic solvents are the aromatic hydrocarbons such as benzene and toluene or the lower aliphatic alcohols such as methyl alcohol.

The compounds of formula 1 wherein X is a (CH$_2$)$_p$CH$_2$ group may also be obtained directly from the compounds of formula 1 wherein X is a (CH$_2$)$_p$CO group by reduction.

As an alternative the compounds 1 wherein X is (CH$_2$)$_p$CH$_2$ are obtained by alkylation of amines of the formula

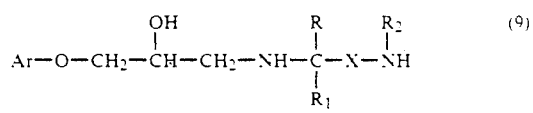

wherein Ar, R, R$_1$ and R$_2$ have the meanings already mentioned, with compounds of the formula

wherein n, R$_3$, R$_4$ and W have the meanings already mentioned.

The reaction is carried out in a suitable inert organic solvent at a temperature of from room temperature to the reflux temperature of the reaction mixture.

The compound of formula 10 are known compounds or may easily be prepared with known techniques.

The compounds of formula 9 wherein X is a (CH$_2$)$_p$—CH$_2$ group are obtained by reduction according to conventional methods of the corresponding amides of formula 9 in which X is (CH$_2$)$_p$CO.

The amides of formula 9 are in turn obtained by condensation of compounds of the formula

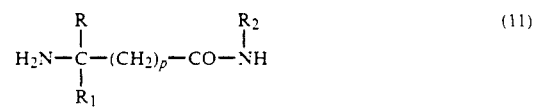

wherein R, R$_1$, R$_2$ and p have the meanings already mentioned, with epoxides of formula (7) or with clorohydrins of formula (8).

The compounds of formula 11 are known compounds or may easily be prepared with known techniques.

The compounds of formula 1 are useful in the pharmaceutical field in cardiovascular therapy as beta-blockers.

Their affinity to the beta-adrenergic receptors has in fact been shown to be at least as good as that of known beta-blockers (see example 14). The compounds according to the invention, unlike known beta-blockers, do not exhibit the latter's side effects on both the systemic and coronary hemodynamic parameters (see example 15).

In addition, the compounds of formula 1 exhibit a calcium antagonistic effect comparable to that of known calcium antagonists, even though their structure is very different, as highlighted in the in vitro test on a rabbit aorta depolarized with $K^+$ (40 mM) and contracted with $CaCl_2$ (7 mM).

In the characterization of the pharmacological profile of the compounds according to the present invention, it is also useful to point out that, unlike both the beta-blockers and the calcium-antagonists, they exhibit an interesting protective action on the cardiac and vascular tissues against ischemic and atherosclerotic damage.

An additional object of the present invention is to provide the pharmaceutical compositions containing, as an active ingredient, the compounds of formula 1 or their pharmaceutically acceptable salts, optionally together with one or more solid or liquid, organic or inorganic, pharmaceutical excipients, such as diluents, preservatives, humidifiers, coloring agents, flavouring agents, etc.. The pharmaceutical compositions of the present invention may be administered in solid pharmaceutical forms, such as tablets, pills, capsules, granules and suppositories, or in liquid pharmaceutical forms such as syrups, suspensions, emulsions and solutions suitable for oral and parenteral administration.

The compounds of the present invention may also be compounded in slow-release pharmaceutical forms.

The preparation of the pharmaceutical compositions of the present invention is accomplished by means of usual techniques.

The amount of compound of formula 1 to be administered may vary depending on several factors, such as the specific activity of the individual compound of formula 1, the therapy and the patient's subjective response as well as on the chosen administration route.

In general, the amount of compound of formula 1 to be administered will be of from 5 mg/kg to 500 mg/kg per day in one or more doses at appropriate intervals.

For the purpose of better illustrating the present invention the following examples are now given. The more significant signals of the $^1H$-NMR spectra are given.

EXAMPLE 1

2-Phthalimido-2-methyl-N-(2,2-diphenylethyl)-N-methyl-propanamide

To a solution of N-methyl-2,2-diphenylethylamine (18 g; 0.085 mol) and of triethylamine (13.6 ml) in methylene chloride (45 ml), keeping the temperature at about 5° C., phthalimidoisobutyrylchloride (23.7 g; 0.095 mol) in methylene chloride (63 ml) is added.

The mixture is stirred for 3 hours at room temperature, the reaction mixture is then washed with water, the organic phase is separated and dried on sodium sulfate. After evaporation of the solvent a crude product is obtained which is purified by chromatography on a silica gel column (eluent, methylene chloride:methyl alcohol=95:5).

2-phthalimido-2-methyl-N-(2,2-diphenylethyl)-N-methyl-propanamide is obtained as a chromatographically pure oil (T.L.C.; eluent, methylene chloride:methyl alcohol:$NH_4OH$=86:10:0.6—detection: iodine vapours, U.V. light 254 nm). $^1H$-NMR (60MHz, $CDCl_3$): delta (ppm): 1.7 (6H, s); 2.5 (3H, s); 4.1 (2H, dd); 4.6 (1H, dd; 7.35 (10H, m); 7.9 (4H, m).

Working in a similar manner the following compounds have been prepared:

2-phthalimido-2-methyl-N-diphenylmethyl-N-methyl-propanamide m.p.=150–152° C. (ethyl alcohol)

2-phthalimido-2-methyl-N-[di-(4-fluorophenyl)-methyl]-N-methyl-propanamide m.p.=169–171° C. (ethyl alcohol)

2-phthalimido-N-diphenylmethyl-N-methyl-propanamide chromatographically pure oil (T.L.C.; eluent, methylene chloride:methyl alcohol=99.1) $^1H$-NMR (60 MHz, $CDCl_3$): delta (ppm): 1.7 (3H, d); 2.8 (3H, s); 5.5 (1H, m); 6.4 (1H, m); 7.0–8.0 14H, m).

2-amino-2-methyl-N-diphenylmethyl-N-methyl-propanamide chromatographically pure oil (T.L.C.; eluent, methylene chloride:methyl alcohol:$NH_4OH$=86:10:0.6) $^1H$-NMR (60 MHz, $CDCl_3$): delta (ppm): 1.5 (6H, s); 7.3 (11H, m).

EXAMPLE 2

2-benzyloxycarbonylamino-2-methyl-N-diphenylmethyl-propanamide

To a solution of 2-benzyloxycarbonylamin-2-methyl-propionic acid (12 g; 0.051 mol) in chloroform (120 ml), a solution of benzidrylamine (9.27 g; 0.051 mol) in chloroform (80 ml) and a solution of dicyclohexylcarbodiimide (15.5 g; 0.075 mol) in chloroform (30 ml) are added.

After 3 hours at the refluxing temperature, the solution is filtered, washed with 5% aqueous HCl, with 5% aqueous NaOH and lastly with water. The organic phase is separated and dried on sodium sulphate and after evaporation of the solvent the crude product is crystallized from ethyl alcohol.

2-benzyloxycarbonylamino-2-methyl-N-diphenylmethyl-propanamide is thus obtained; m.p.=157–159° C.

IR and $^1H$-NMR spectra are consistent with the assigned structure.

EXAMPLE 3

2-amino-2-methyl-N-(2,2-diphenylethyl)-N-methyl-propanamide

To a solution of 2-phthalimido-2-methyl-N-(2,2-diphenylethyl)-N-methyl-propanamide (24 g; 0.056 mol) prepared as described in Example 1, in isopropanol (500 ml) and water (100 ml), sodium borohydride (10.8 g; 0.28 mol) is added and left under stirring at room temperature for 24 hours.

The solution is concentrated to a small volume, diluted with glacial acetic acid (80 ml) and kept under stirring for 2 hours at 100° C.

After evaporation of the solvent, the obtained residue is treated with 10% ammonia. After extraction with methylene chloride, the organic phase is separated and dried on sodium sulphate.

By evaporation of the solvent, 2-amino-2-methyl-N-(2,2-diphenylethyl)-N-methyl-propanamide is obtained as a chromatographically pure oil (T.L.C.; eluent, methylene chloride:methyl alcohol:NH$_4$OH = 86:10:0.6). $^1$H-NMR (60 MHz, CDCl$_3$): delta (ppm): 1.8 (6H, s); 2.8 (3H, s); 4.2 (3H, m); 7.2 (10H, s).

Working in a similar manner the following compounds have been prepared:

2-amino-2-methyl-N-diphenylmethyl-N-methyl-propanamide chromatographically pure oil (T.L.C.; eluent, methylene chloride:methyl alcohol:NH$_4$OH = 86:10:0.6) $^1$H-NMR (60 MHz, CDCl$_3$): delta (ppm): 1.5 (6H, s); 3.0 (3H, s); 7.3 (11H, m).

2-amino-2-methyl-N-[di-(4-fluorophenyl-methyl]-N-methyl-propanamide chromatographically pure oil (T.L.C.; eluent, methylene chloride:methyl alcohol:NH$_4$OH = 86:10:0.6) $^1$H-NMR ($\alpha$MHz, CDCl$_3$): delta (ppm): 1.8 (6H, d); 2.8 (3H, s); 7.2 (11H, m).

2-amino-N-diphenylmethyl-N-methyl-propanamide chromatographically pure oil (T.L.C.; eluent, methylene chloride:methyl alcohol:NH$_4$OH = 86:10:0.6) $^1$H-NMR (60 MHz, CDCl$_3$): delta (ppm): 1.1 (3H, d); 1.5 (2H, s); 2.0 (3H, s); 3.0 (1H, m); 4.4 (1H, s); 7.4 (10H, m).

EXAMPLE 4

2-amino-2-methyl-N-diphenylmethyl-propanamide

A solution of 2-benzyloxycarbonylamino-2-methyl-N-diphenylmethyl-propanamide (10 g; 0.025 mol), prepared as described in Example 2, in ethyl alcohol saturated with hydrochloric acid (200 ml) is heated at the reflux temperature for 6 hours.

After evaporation of the solvent, the residue is treated with ethyl ether, washed with 5% aqueous NaOH and lastly with water.

The organic layer is dried on sodium sulphate and evaporated, 2-amino-2-methyl-N-diphenylmethyl-propanamide is obtained as a chromatographically pure oil (T.L.C.; eluent, methylene chloride:methyl alcohol:NH$_4$OH = 86:10:0.6). $^1$H-NMR (60 MHz, CDCl$_3$): delta (ppm): 1.35 (1H, s); 7.35 (10H, m).

EXAMPLE 5

2-amino-2-methyl-N-(2,2-diphenylethyl)-N-methyl-propylamine

To a suspension of 2-amino-2-methyl-N-(2,2-diphenylethyl)-N-methyl-propanamide (14 g; 0.047 mol), prepared as described in Example 3, and of sodium borohydride (5.39 g; 0.14 mol) in tetrahydrofuran (144 ml), kept at 5° C. in a nitrogen atmosphere, boron etherate trifluoride (23.76 ml) is added.

The reaction mixture is kept under stirring at 40° C. for 2 hours and then cooled to 5° C.

The excess of hydride is decomposed by carefully adding HCl 6N (50 ml) and heating for 2 hours at the reflux temperature.

After evaporation of the solvent, the residue is treated with dilute ammonia and extracted with methylene chloride.

The organic phase is dried on sodium sulphate obtaining, after evaporation of the solvent, 2-amino-2-methyl-N-(2,2-diphenylethyl)-N-methyl-propylamine as a chromatographically pure oil (T.L.C.; eluent, methylene chloride:methyl alcohol:NH$_4$OH = 86:10:0.6). $^1$H-NMR (60 MHz, CDCl$_3$): delta (ppm): 1.1 (6H, s); 3.0 (3H, s); 3.5 (2H, s); 3.8 (2H, d); 4.8 (1H, t); 7.0 (10H, s).

Working in a similar manner the following compounds have been prepared:

2-amino-2-methyl-N-diphenylmethyl-N-methyl-propylamine dihydrochloride m.p. = 148–150° C. (ethyl alcohol)

2-amino-N-diphenylmethyl-N-methyl-propylamine oil (T.L.C.; eluent, methylene chloride:methyl alcohol:NH$_4$OH = 86:10:0.6) $^1$H-NMR (60 MHz, CDCl$_3$): delta (ppm): 1.1 (6H, s); 2.4 (2H, s); 2.5 (3H, s); 3.0 (2H, d); 4.6 (1H, t); 7.0 (10H, bs).

2-amino-2-methyl-N-diphenylmethyl-propylamine oil (T.L.C.; eluent, methylene chloride:methyl alcohol:NH$_4$OH = 86:10:0.6) $^1$H-NMR (60 MHz, CDCl$_3$): delta (ppm): 1.1 (6H, s); 3.0 (3H, s); 4.1 (2H, ddd); 4.5 (1H, dd); 7.4 (10H, m).

EXAMPLE 6

N-(3,3-diphenylpropyl)-N-methyl-2-methyl-2-nitro-propylamine

To a suspension of (3,3-diphenylpropyl)-methylamine (10 g; 0.044 mol) in aqueous formaldehyde (8.5 ml) cooled to 10° C., 2-nitropropane (9 g; 0.1 mol) is added.

The mixture is kept under stirring at room temperature for 1 hour and then diluted with a saturate aqueous solution of sodium chloride.

The organic phase is separated and dried on sodium sulphate. The residue obtained after evaporation of the solvent is purified by cromatography on a silica gel column (eluent, methylene-chloride).

N-(3,3-diphenylpropyl)-N-methyl-2-methyl-2-nitro-propylamine as a chromatographically pure oil is obtained (T.L.C.; eluent, methylene chloride). $^1$H-NMR (60 MHz, CDCl$_3$): delta (ppm): 1.35 (6H, s); 2.15 (7H, m); 2.6 (3H, s); 4.0 (1H, t); b 7.2 (10H, m).

EXAMPLE 7

2-amino-2-methyl-N-(3,3-diphenylpropyl)-N-methyl-propylamine dihydrochloride

A suspension of N-(3,3-diphenylpropyl)-N-methyl-2-methyl-2-nitropropylamine (8 g; 0.025 mol), prepared as described in Example 6, and of 10% palladium on carbon (3 g) in absolute ethyl alcohol (500 ml), is hydrogenated at 50° C. under hydrogen pressure (50 atm).

When the absorption of hydrogen is over, the catalyst is filtered and the obtained solution is evaporated to dryness.

The residue is dissolved in ethyl alcohol saturated with hydrochloric acid and the 2-amino-2-methyl-N-(3,3-diphenylpropyl-N-methyl-propylamine is thus separated under the form of dihydrochloride (m.p. = 75–77° C.).

IR and $^1$H-NMR spectra are consistent with the assigned structure.

EXAMPLE 8

2-Phthalimido-N-diphenylmethyl-N-methyl-ethylamine

A solution of N-(2-chloroethyl)-N-diphenylmethyl-N-methylamine (12 g; 0.046 mol) and of potassium phthalimide (10 g; 0.054 mol) in dimethylformamide (50 ml) is kept under stirring for 5 hours at 90° C.

The reaction mixture is then cooled and extracted with chloroform, dried on sodium sulphate and evaporated to dryness.

The obtained residue, crystallized from ethyl ether, yields 2-phthalimido-N-diphenylmethyl-N-methyl-ethylamine, m.p.=130-131° C.

IR and ¹H-NMR spectra are consistent with the assigned structure.

EXAMPLE 9

2-Amino-N-diphenylmethyl-N-methyl-ethylamine

To a solution of 2-phthalimido-N-diphenylmethyl-N-methyl-ethylamine (17 g; 0.046 mol), prepared as described in Example 8, in methyl alcohol (200 ml) hydrazine is added (6 ml).

The reaction mixture is maintained at the reflux temperature for 1 hour, it is then cooled and the solvent is evaporated.

concentrate hydrochloric acid is added to the thus obtained residue and the mixture is heated under stirring for 1 hour at 100° C.

After cooling, the suspension is filtered and the obtained solution is evaporated to dryness giving a chromatographically pure oil, 2-amino-N-diphenylmethyl-N-methyl-ethylamine (T.L.C.; eluent, methylene chloride:methyl alcohol:NH₄OH=86:10:0.6). ¹H-NMR (60 MHz, CDCl₃): delta (ppm): 2.2 (3H, s); 2.5 (2H, d); 2.7 (2H, d); 4.5 (1H, s); 7.3 (10H, m).

EXAMPLE 10

2-[2-hydroxy-3-(2-methoxyphenoxy)-propylamino]-2-methyl-N-(2,2-diphenylethyl)-N-methyl-propylamine dihydrochloride A solution of 2-amino-2-methyl-N-(2,2-diphenylethyl)-N-methyl-propylamine (10 g; 0.035 mol) prepared as described in Example 5, and of 1,2-epoxy-3-(2-methoxyphenoxy)-propane (7.6 g; 0.024 mol) in anydrous toluene (100 ml) is refluxed for 4 hours.

By evaporation of the solvent a residue is obtained which is purified by chromatography on a silica gel column (eluent, methylene chloride:methyl alcohol=95.5).

2-[2-hydroxy-3-(2-methoxyphenoxy)-propylamino]-2-methyl-N-(2,2-diphenylethyl)-N-methyl-propylamine is obtained which, after dissolution in ethyl acetate and treatment with a saturate solution of hydrochloric acid in ethyl ether, precipitates by cooling as dihydrochloride salt; m.p.=170-172° C.

IR and ¹H-NMR spectra are consistent with the assigned structure.

Working in a similar manner the following compounds have been prepared:

2-[2-hydroxy-3-(2-methoxyphenoxy)-propylamino]-2-methyl-N-diphenylethyl-N-methyl-propylamine dihydrochloride m.p.=90-93° C. (ethyl acetate)

2-[2-hydroxy-3-(2-cyanophenoxy)-propylamino]-2-methyl-N-diphenylmethyl-N-methyl-propylamine dihydrochloride m.p.=175-177° C. (ethyl acetate)

2-{2-hydroxy-3-[4-(2-methoxyethyl)-phenoxy]-propylamino}-2-methyl-N-diphenylmethyl-N-methyl-propylamine dihydrochloride m.p.=155-157° C. (ethyl acetate)

2-[2-hydroxy-3-(4-carbamoylmethylphenoxy)-propylamino]-2-methyl-N-diphenylmethyl-N-methyl-propylamine dihydrochloride m.p.=153-155° C. (ethyl acetate)

2-[2-hydroxy-3-(4-phenylmethoxy-phenoxy)-propylamino]-2-methyl-N-diphenylmethyl-N-methyl-propylamine chromatographically pure oil (T.L.C.; eluent, methylene chloride:methyl alcohol:NH₄OH=86:10:0.6)

¹H-NMR (60 MHz, CDCl₃): delta (ppm): 1.2 (6H, s); 2.35 (3H, s); 2.5 (2H, s); 4.9 (1H, bs); 5.1 (2H, bs); 6.95 (4H, bs); 8.4 (15H, m).

2-[2-hydroxy-3-(2-methoxyphenoxy)-propylamino]-N-diphenylmethyl-N-methyl-propylamine dihydrochloride m.p.=162-164° C. (ethyl acetate) 2-[2-hydroxy-3-(2-methoxyphenoxy)-propylamino]-2-methyl-N-diphenylmethyl-propylamine dihydrochloride m.p.=140-145° C. (ethyl alcohol)

2-[2-hydroxy-3-(2-methoxyphenoxy)-propylamino]-2-methyl-N-(3,3-diphenylpropyl)-N-methyl-propylamine dihydrochloride m.p.=75° C. (ethyl alcohol)

N-{2-]2-hydroxy-3-(2-methoxyphenoxy)-propylamino]-ethyl}-N-methyl-(3,3-diphenyl-propylamine dihydrochloride m.p.=163-165° C. (ethyl acetate)

2-]2-hydroxy-3-(2-methoxyphenoxy)-propylamino]-N-diphenylmethyl-N-methyl-ethylamine dihydrochloride m.p.=78° C. (ethyl alcohol)

2-]2-hydroxy-3-(2-methoxyphenoxy)-propylamino]-2-methyl-N-diphenylmethyl-N-methyl-propanamide dihydrochloride m.p.=155° C. (ethyl acetate)

2-]2-hydroxy-3-(2-methoxyphenoxy)-propylamino]-2-methyl-N-[di-(4-fluorophenyl)-methyl]-N-methyl-propanamide chromatographically pure oil (T.L.C.; eluent, methylene chloride:methyl alcohol:NH₄OH=86:10:0.6) ¹H-NMR (60 MHz, CDCl₃): delta (ppm): 1.1 (6H, s), 2.3 (3H, s); 3.8 (3H, s); 6.8-7.4 (12H, m).

2-[2-hydroxy-3-(2-methylthiophenoxy)propylamino]-2-methyl-N-diphenylmethyl-N-methylpropylamine dihydrochloride m.p.=161-164° C. 2-[2-hydroxy-3-(2-allylphenoxy)-propylamino]-2-methyl-N-diphenyl-N-methyl-propylamino dihydrochloride m.p. 169-171° C.

2-[2-hydroxy-3-(2-allyloxyphenoxy)propylamino]-2-methyl-N-diphenylmethyl-N-methylpropylamine dihydrochloride, solid compound having a not well defined melting point—chromatographically pure (T.L.C.; eluent, methylene chloride:methyl alcohol:NH$_4$OH = 86:10:0.6)

2-[2-hydroxy-3-(2-allyloxyphenoxy)propylamino]-2-methyl-N-(3,3-diphenylpropyl)-N-methylpropylamine dihydrochloride, solid compound having a not well defined melting point—chromatographically pure (T.L.C.; eluent, methylene chloride:methyl alcohol:NH$_4$OH = 86:10:0.6)

2-[2-hydroxy-3-(4-methoxyphenoxy)propylamino]-2-methyl-N-diphenylmethyl-N-methylpropylamine dihydrochloride m.p. 156–158° C.

2-[2-hyroxy-3-(1-naphthyloxy)propylamino]-2-methyl-N-diphenylmethyl-N-methylpropylamine dihydrochloride m.p. 159–161° C.

2-[2-hydroxy-3-(2-carbazolyloxy)propylamino]-2-methyl-N-diphenylmethyl-N-methylpropylamine, chromatographically pure oil (T.L.C.; eluent, methylene chloride:methyl alcohol:NH$_4$OH = 86:10:0.6)

EXAMPLE 11

2-[2-hydroxy-3-(2-methoxyphenoxy)-propylamino]-2-methyl-N-[di-(4-fluorophenyl)-methyl]-N-methylpropylamine dihydrochloride Working according to the method described in Example 5 but replacing the 2-amino-2-2-methyl-N-(2,2-diphenylethyl)-N-methyl-propanamide with an equivalent amount of 2-[2-hydroxy-3-(2-methoxyphenoxy)-propylamino]-2-methyl-N-[di-(4-fluorophenyl)-methyl]-N-methyl-propanamide prepared as described in Example 10, 2-[2-hydroxy-3-(2-methoxyphenoxy)-propylamino]-2-methyl-N-[di-(4-fluorophenyl)-methyl]-N-methyl-propylamine is obtained as a dihydrochloride salt monohydrate; m.p. = 130–135° C. (ethyl alcohol).

IR and $^1$H-NMR spectra are consistent with the assigned structure

Working in a similar manner the following compounds have been prepared:

2-[2-hydroxy-3-(2-methoxyphenoxy)-propylamino]-2-methyl-propylamine chromatographically pure oil (T.L.C.; eluent, methylene chloride:methyl alcohol:NH$_4$OH = 86:10:0.6) $^1$H-NMR (300 MHz, CDCL$_3$): delta (ppm): 1.0 (6H, s); 2.6 (2H, s); 2.7 (1H, dd); 2.8 1H, dd); 3.85 (3H, s); 4.1 (3H, m); 6.9 (4H, m).

2-[2-hydroxy-3-(2-methoxyphenoxy)-propylamino]-2-methyl-N-methyl-propylamine chromatographically pure oil (T.L.C.; eluent, methylene chloride:methyl alcohol:NH$_4$OH = 86:10:0.6)
Mass (CI isobutane PPNICI:M+ 283.

2-[2-hydroxy-3-(2-methoxyphenoxy)-propylamino]-2-methyl-propanamide chromatographically pure oil (T.L.C.; eluent, methylene chloride:methyl alcohol:NH$_4$OH = 86:10:0.6)

$^1$H-NMR (60 MHz, CDCl$_3$): delta (ppm): 1.4 (6H, s); 3.8 (3H, s); 4.0 (2H, s); 7.0 (4H, s).

2-[2-hydroxy-3-(2-methoxyphenoxy)-propylamino]-2-methyl-N-methyl-propanamide chromatographically pure oil (T.L.C.; eluent, methylene chloride:methyl alcohol:NH$_4$OH = 86:10:0.6)
$^1$H-NMR (60 MHz, CDCl$_3$): delta (ppm): 1.2 (6H, s); 4.0 (3H, s); 4.2 (2H, s); 7.0 (4H, s).
Mass (CI isobutane PPNICI: M+ 297.

2-[2-hydroxy-3-(4-hydroxyphenoxyl)-propylamino]-2-methyl-N-diphenylmethyl-N-methyl-propylamine dihydrochloride A solution of b 2-[2-hydroxy-3-(4-phenylmethoxyphenoxy)-propylamino]-2-methyl-N-diphenylmethyl-N-methyl-propylamine dihydrochloride (5 g; 0.0084 mol), prepared as described in Example 10, in ethyl alcohol saturated with hydrochloric acid (50 ml) is refluxed for 6 hours.

The mixture is then evaporated to dryness and the residue is dissolved in methylene chloride, washed with dilute ammonia and evaporated to dryness.

The crude product obtained is purified by chromatography on a silica gel column (eluent, methylene chloride:methyl alcohol = 97:3) to yield 2-[2-hydroxy-3-(4-hydroxyphenoxy)-propylamino]-2-methyl-N-diphenylmethyl-N-methyl-propylamine which by treatment with ethyl alcohol saturated with hydrochloric acid and subsequent crystallization from ethyl acetate gives the dihydrochloride salt. (m.p. = 148–150° C.).

IR and $^1$H-NMR spectra are consistent with the assigned structure.

EXAMPLE 13

2-[2-hydroxy-3-(2-methoxyphenoxy)-propylamino]-2-methyl-N-diphenylmethyl-N-methyl-propylamine dihydrochloride A solution of 2-[2-hydroxy-3-(2-methoxyphenoxy)-propylamino-2-methyl-propylamine (2 g; 0.0075 mol), prepared as described in Example 11, and benzidrylchloride (133 ml) in acetonitrile (20 ml) is kept at 80° C. for 15 hours.

The residue is treated with ethyl acetate, washed with water, dried on sodium sulphate and evaporated.

The crude product obtained is dissolved in ethyl acetate and treated with ethyl ether saturated with HCl. The 2-[2-hydroxy-3-(2-methoxyphenoxy)-propylamino]-2-N-diphenylmethyl-N-methyl-propylamine dihydrochloride is thus separated, m.p. = 90–93° C.

Working in a similar manner the following compound has been prepared:

2-[2-hydroxy-3-(2-methoxyphenoxy)-propylamino]-2-methyl-N-diphenylmethyl-propylamine dihydrochloride m.p. = 140–145° C. (ethyl alcohol)

2-[2-hydroxy-3-(2-methoxyphenoxy)-propylamino]-2-methyl-N-[(2-nitrophenyl)-phenylmethyl]-N-methyl-propylamine chromatographically pure oil (T.L.C. - eluent, methylene chloride:methyl alcohol:NH$_4$OH = 86:10:0.6)

2-[2-hydroxy-3-(2-methoxyphenoxy)-propylamino]-2-
methyl-N-[3,3-di-(4-methoxyphenyl)
propyl]-N-methylpropylamine chromatographically pure oil (T.L.C. - eluent, methylene chloride:methyl alcohol:NH₄OH = 86:10:0.6)

2-[2-hydroxy-3-(2-methoxyphenoxy)-propylamino]-2-
methyl-N-[3,3-di-(4-methylphenyl)propyl]-N-methyl-
propylamine chromatographically pure oil (T.L.C. - eluent, methylene chloride:methyl alcohol:NH₄OH = 86:10:0.6)

2-[2-hydroxy-3-(2-methoxyphenoxy)-propylamino]-2-
methyl-N-[3,3-di-(4-chlorophenyl)propyl]-N-methyl-
porpylamine chromatographically pure oil (T.L.C. - eluent, methylene chloride:methyl alcohol:NH₄OH = 86:10:0.6)

EXAMPLE 14

The compound 3-[2-hydroxy-3-(2-methoxyphenoxy)-propylamino]-2-methyl-N-diphenylmethyl-N-methylpropylamine dihydrochloride (hereinafter referred to as compound A) has been studies in vitro to evaluate the affinity to receptors $\beta_1$ and $\beta_2$ by means of receptor binding on isolate heart and lung membranes.

The antagonistic activity on tachycardia induced by isopropylnoradrenaline on guinea pig atria has also been evaluated.

The results are given in Table 1.

TABLE 1

Affinity to $\beta_1$ and $\beta_2$ adrenergic receptors and antagonism of isopropylnoradrenaline (ISO).

| | RECEPTOR BINDING | | |
|---|---|---|---|
| | $\beta_1$ $K_i$ μM | $\beta_2$ $K_i$ μM | Anti-ISO $\beta_1$ IC$_{50}$ μM |
| Compound A | 0.011 | 0.010 | 0.07 |
| Propranolol | 0.004 | 0.005 | 0.01 |

The data given in Table 1 show that the compound A has a high affinity toward the $\beta_1$ and $\beta_2$ receptors comparable to that of Propranolol, a known beta-blocker used in therapy.

The antagonistic activity of isopropylnoradrenaline is also high and comparable to that of Propranolol.

EXAMPLE 15

The compound A (see Example 14) has been studied after intravenous administration to the anesthetized dog to evaluate the effects on the systemic and coronary hemodynamics.

The compound A administered by intravenous route at does of 250 and 500 μg/kg has reduced the systemic blood pressure without inducing significant effects on the heart rate and on the cardiac contractility expressed as dP/dt.

The results are shown in Table 1.

The compound A administered at a does of 0.25 mg/kg has induced a reduction of the peripheral and coronary vascular resistance accompanied by an increase of the cardiac output and of the coronary flow.

The results are shown in Table 3.

It has been proved that Propranolol has opposite effects on the hemodynamic parameters because it increases both the coronary resistances and the systemic resistances and depresses at the same time the cardiac output and the coronary flow (D.H. McKenna et al., Circulation Res., XIX, 1966, 520; L.S. Whitsitt, B.R. Lucchesi, Circulation Res., XXI, 1967, 305).

TABLE 2

Effects of Compound A on blood pressure, heart rate and myocardial contractility (dP/dt) in the anesthetized dog

| | Heart rate (beats/min) | Blood pressure (mm Hg) | | | L.H. ventricular pressure (mm Hg) | dP/dt P.V.S. (mm Hg/sec) | Contractility Index $\dfrac{dP/dt}{P}$ (sec$^{-1}$) | Interval P-R ECG (msec) |
|---|---|---|---|---|---|---|---|---|
| | | Mx | Md | Mn | | | | |
| Basal | 158 | 165 | 128 | 107 | 142 | 3310 | 48.4 | 90.4 |
| Compound A 250 μg/kg i.v. | 164 | 162 | 124 | 100 | 141 | 3512 | 51.5 | 95.2 |
| Basal | 153 | 164 | 126 | 104 | 141 | 3341 | 49.4 | 92.6 |
| Compound A 500 μg/kg i.v. | 162 | 160 | 118 | 93 | 140 | 3626 | 54.0 | 95.9 |

TABLE 3

Effects of Compound A on the systemic and coronary hemodynamics in the anaesthetized dog.

| | Heart rate (beats/min) | Blood pressure (mm Hg) | | | Coronary flow (ml/min) | Coronary resistances (mmHg/ml/min) | Cardiac output (l/min) | Cardiac work (l.atm/min) | Total Perif. Resistances (mmHg/l/min) |
|---|---|---|---|---|---|---|---|---|---|
| | | Mx | Md | Mn | | | | | |
| Basal | 150 | 143 | 112 | 97 | 40.1 | 2.793 | 1.972 | 0.291 | 56.8 |
| Compound A 250 μg/kg i.v. | 150 | 141 | 106 | 88 | 54.0 | 1.963 | 2.433 | 0.339 | 43.6 |

We claim:

1. A compound of the formula

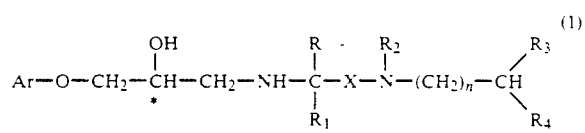

wherein

Ar is a cyclic or bicyclic aromatic system optionally substituted by one or more substituents selected from the group consisting of halogen, hyroxy, $C_1$-$C_5$ alkyl, $C_2$-$C_5$ alkenyl, $C_1$-$C_5$ alkoxy, $C_1$-$C_3$ alkylthio, $C_2$-$C_5$ alkenyloxy, or alkoxy-alkyl having from 1 to 5 carbon atoms both in the alkyl and in the alkoxyl portion, phenoxy or phenylalkoxy group, aminocarbonylalkyl group having from 1 to 3 carbon atoms in the alkyl portion, cyano, carboxy, aminocarbonyl or amino group, piperazinyl, piperidinyl, and morpholinyl groups;

R and $R_1$, equal to or different from one another, are hydrogen or $C_1$-$C_3$ alkyl;

X is a $(CH_2)_pY$ group wherein Y is a methylene group or a carbonyl group and p is an integer selected from among 0, 1 and 2;

$R_2$ is hydrogen or $C_1$-$C_3$ alkyl;

n is an integer selected among 0, 1 and 2;

$R_3$ and $R_4$, equal to or different from one another, are phenyl optionally substituted by one or more halogen, $C_1$-$C_3$ alkyl, $C_1$-$C_3$ alkoxy, nitro, alkylthio, alkylsulfinyl and alkylsulfonyl groups, having from 1 to 3 carbon atoms in the alkyl portion;

and their salts with pharmaceutically acceptable acids or bases.

2. A compound according to claim 1 wherein Ar is an aromatic system selected from the group consisting of phenyl, naphthyl, tetrahydronaphthyl, idenyl, all of which are optionally substituted by one or more substituents selected among chlorine, fluorine or bromine, and allyl, methyl, phenyl, methoxy, allyloxy, cyano, carbamoylmethyl, hydroxy, acetyl, cyclohexyl, methoxyethyl, and methylthio.

3. A compound according to claim 1 wherein Ar is an aromatic system selected from the group consisting of 2-methoxyphenyl, 2-allyloxyphenyl, 2-cyanophenyl, 2-methylphenyl, 2-allylphenyl, 4-carbamoylmethylphenyl, and 4-hydroxyphenyl.

4. A compound according to any one of the claims from 1 to 3 wherein R and $R_1$, equal to or different from one another, are hydrogen or methyl; $R_2$ is hydrogen or methyl; $R_3$ and $R_4$, equal to or different from one another, are phenyl optionally substituted by a fluorine atom.

5. A pharmaceutical composition containing a therapeutically effective amount of a compound according to claim 1 together with one or more pharmaceutically acceptable excipients.

* * * * *